US010946085B2

(12) United States Patent
Collado Gimbert et al.

(10) Patent No.: US 10,946,085 B2
(45) Date of Patent: Mar. 16, 2021

(54) *STREPTOCOCCUS UBERIS* EXTRACT AS AN IMMUNOGENIC AGENT

(71) Applicant: HIPRA SCIENTIFIC, S.L.U., Amer (ES)

(72) Inventors: Rosa Maria Collado Gimbert, Girona (ES); Antoni Prenafeta I Amargós, Amer (ES)

(73) Assignee: HIPRA SCIENTIFIC, S.L.U., Amer (ES)

( * ) Notice: Subject to any disclaimer, the term of this patent is extended or adjusted under 35 U.S.C. 154(b) by 0 days.

(21) Appl. No.: 16/075,092

(22) PCT Filed: Feb. 14, 2017

(86) PCT No.: PCT/EP2017/053306
§ 371 (c)(1),
(2) Date: Aug. 2, 2018

(87) PCT Pub. No.: WO2017/140683
PCT Pub. Date: Aug. 24, 2017

(65) Prior Publication Data
US 2019/0038736 A1    Feb. 7, 2019

(30) Foreign Application Priority Data

Feb. 15, 2016 (EP) .................................. 16382060

(51) Int. Cl.
| *A61K 39/09* | (2006.01) |
| *C12N 1/36* | (2006.01) |
| *C12N 1/20* | (2006.01) |
| *A61P 31/04* | (2006.01) |
| *A61K 9/00* | (2006.01) |
| *A61K 39/39* | (2006.01) |
| *A61K 35/00* | (2006.01) |

(52) U.S. Cl.
CPC .......... *A61K 39/092* (2013.01); *A61K 9/0019* (2013.01); *A61K 39/39* (2013.01); *A61P 31/04* (2018.01); *C12N 1/20* (2013.01); *C12N 1/36* (2013.01); *A61K 35/00* (2013.01)

(58) Field of Classification Search
None
See application file for complete search history.

(56) References Cited

FOREIGN PATENT DOCUMENTS

| WO | WO 96/41879 A1 | 12/1996 |
| WO | WO 01/96381 A2 | 12/2001 |
| WO | WO 2008/153541 A1 | 12/2008 |
| WO | WO 2010/041056 A1 | 4/2010 |
| WO | WO 2012/116447 A1 | 9/2012 |
| WO | WO 2012/152898 A1 | 11/2012 |
| WO | WO 2015/042449 A2 | 3/2015 |

OTHER PUBLICATIONS

International Search Report and Written Opinion dated Sep. 14, 2017 for PCT Application No. PCT/EP2017/053306, 20 pages.
Koen Breyne et al., "Preconditioning with Lipopolysaccharide or Lipoteichoic Acid Protects against *Staphylococcus aureus* Mammary Infection in Mice", Frontiers in Immunology, Jul. 24, 2017, vol. 8, Article 833, pp. 1-16.
Brown, Stephanie, et al., "Wall Teichoic Acids of Gram-Positive Bacteria", The Annual Review of Microbiology 2013, vol. 67, pp. 313-336.
Czabańska, Anna, et al., "Structural analysis of the lipoteichoic acids isolated from bovine mastitis *Streptococcus uberis* 233, *Streptococcus dysgalactiae* 20333 and *Streptococcus agalactiae* 0250", Carbohydrate Research, Sep. 15, 2012, vol. 361, pp. 200-205.
Deb, Rajib, et al., "Trends in diagnosis and control of bovine mastitis: a Review", Pakistan Journal of Biological Sciences 2013, vol. 16, No. 23, pp. 1653-1661.
Denis, M., et al., "Vaccines against bovine mastitis in the New Zealand context: what is the best way forward?", New Zealand Veterinary Journal 2009, vol. 57, No. 3, pp. 132-140.
Finch, Julie, et al. "Local vaccination with killed *Streptococcus uberis* protects the bovine mammary gland against experimental intramammary challenge with the homologous strain", Infection and Immunity, Sep. 1994, vol. 62, No. 9, pp. 3599-3603.
Günther, Juliane, et al., "*Streptococcus uberis* strains isolated from the bovine mammary gland evade immune recognition by mammary epithelial cells, but not of macrophages", Veterinary Research 2016, vol. 47, No. 13, pp. 1-14.
Hill, A.W., et al., "Immune modification of the pathogenesis of *Streptococcus uberis* mastitis in the dairy cow", FEMS Immunology and Medical Microbiology 1994, vol. 8, pp. 109-117.
Leigh, J.A., et al., "Vaccination with the plasminogen activator from *Streptococcus uberis* induces an inhibitory response and protects against experimental infection in the dairy cow", Vaccine 1999, vol. 17, pp. 851-857.
Moore, Glenis E., et al., "Biofilm production by *Streptococcus uberis* associated with intramammary infections", May 2009, University of Tennessee Honors Thesis Projects, pp. 1-14.
Perez M.M., et al., "Protection from *Staphylococcus aureus* mastitis associated with poly-N-acetyl beta-1,6 glucosamine specific antibody production using biofilm-embedded bacteria", Vaccine Feb. 12, 2009, vol. 27, No. 17, pp. 2379-2386.

(Continued)

*Primary Examiner* — Jennifer E Graser
(74) *Attorney, Agent, or Firm* — Squire Patton Boggs (US) LLP

(57) ABSTRACT

The present invention relates to an extract of *Streptococcus uberis* as an immunogenic agent. It also relates to a process for obtaining said agent which comprises incubating a biofilm-producing *S. uberis* strain to obtain a biofilm and thermally treating the biofilm obtained. It relates also to a pharmaceutical composition comprising teichoic acids, preferably lipoteichoic acids, for use in the prevention and/or treatment of mastitis and/or infections caused by *Streptococcus* sp. or by biofilm-producing bacteria. The present invention also relates to a vaccine which comprises said immunogenic agent and to said vaccine and immunogenic agent for use in the prevention and/or treatment of infections caused by *Streptococcus* sp., especially in the prevention and/or treatment of mastitis caused by *S. uberis*. It also relates to a vaccination kit which comprises said agent or vaccine.

9 Claims, 5 Drawing Sheets

(56) References Cited

OTHER PUBLICATIONS

Prado, M.E., et al., "Vaccination of dairy cows with recombinant *Streptococcus uberis* adhesion molecule antibodies that reduce adherence to and internalization of *S. uberis* into bovine mammary epithelial cells", Veterinary Immunology and Immunopathology 2011, vol. 141, pp. 201-208.
Remington The Science and Practice of Pharmacy, 20$^a$ edition, Lippincott Williams & Wilkins, Filadelfia, 2000 [ISBN: 0-683-306472].
Rowe, Raymond C. et al. (eds.), "Handbook of Pharmaceutical Excipients", 4th edition, Pharmaceutical Press 2003 [ISBN: 0-85369-472-9].
Stepanović, Srdjan, et al., "Quantification of biofilm in microtiter plates: Overview of testing conditions and practical recommendations for assessment of biofilm production by staphylococci", APMIS 2007, vol. 115, pp. 891-899.
Sutherland, Ian W., "The biofilm matrix—an immobilized but dynamic microbial environment", Trends in Microbiology May 2001, vol. 9, No. 5, pp. 222-227.
Wedlock, D. Neil, et al, "Dairy cows produce cytokine and cytotoxic T cell responses following vaccination with an antigenic fraction from *Streptococcus uberis*", Veterinary Immunology and Immunopathology 2014, vol. 160, pp. 51-60.
Weidenmaier, Christopher, et al., "Teichoic acids and related cell-wall glycopolymers in Gram-positive physiology and host interactions", Nature Reviews Microbiology Apr. 2008, vol. 6, pp. 276-287.

US 10,946,085 B2

STREPTOCOCCUS UBERIS EXTRACT AS AN IMMUNOGENIC AGENT

CROSS-REFERENCE TO RELATED APPLICATIONS

This application is a filing under 35 U.S.C. § 371 of International Patent Application No. PCT/EP2017/053306, filed Feb. 14, 2017, which claims priority to European Patent Application No. 16382060.8, filed Feb. 15, 2016. Each of the foregoing applications is incorporated herein by reference in its entirety.

FIELD OF THE INVENTION

The present invention relates to the field of vaccines and specifically relates to a novel immunogenic agent based on *S. uberis* bacterium and to compositions containing teichoic acids for its use in vaccine compositions for the prevention and/or treatment of mastitis and infections caused by *Streptococcus* sp. and by biofilm-producing bacteria, especially in bovine livestock.

BACKGROUND ART

Mastitis is a pathology generally caused by a bacterial infection which is characterized by inflammation of the mammary gland and which extensively affects livestock in general, particularly bovine, ovine and goat, the incidence thereof being particularly significant in dairy cows, since it involves significant economic losses for the milk industry at a global level.

The clinical signs of mastitis may vary from the appearance of some visible abnormalities in the milk, such as protein aggregates or coagulates, possibly accompanied by pain and inflammation of the mammary gland, to the production of a secretion mainly made of protein aggregates, bacteremia, septicemia and even the death of the animal may occur. Mastitis may also be present in subclinical form such that the inflammation of the mammary gland does not create visible changes in the milk or udder, although the subclinically infected cows produce less milk and of lower quality.

Mastitis may be caused by different pathogens, those which stand out include species of the genus *Staphylococcus* and of the genus *Streptococcus*, in particular *Streptococcus uberis* (hereinafter *S. uberis*). *S. uberis* is a Gram-positive bacterium with a cell wall similar to that of *Staphylococcus* sp., as well as that of *Streptococcus* sp., among those which *S. agalactiae* and *S. dysgalactiae* also stand out. *S. uberis* is the pathogen more commonly isolated from clinical and subclinical cases of mastitis within the genus *Streptococcus*. In recent decades, it has become one of the main causes of clinical and subclinical mastitis in most parts of the world. *S. uberis* is considered an environmental bacterium, difficult to combat since it is capable of surviving and replicating both inside and outside the udder and is very widespread in cattle installations. Other pathogens causing mastitis are *S. dysgalactiae*, *Staphylococcus aureus*, *S. agalactiae*, *Mycoplasma bovis*, *Klebsiella pneumoniae* and *Escherichia coli*, among others.

At present, different strategies are pursued to prevent mastitis or even to reduce its incidence or to mitigate its effects. Mainly, the prevention strategies are focused on improving hygiene and the milking procedures, while treatment with antibiotics is the preferred option for the therapeutic approach.

Furthermore, in recent years, interest has grown in developing preventive strategies based on administering vaccines and, in this sense, different immunogenic agents based on *S. uberis* have been described in the state of the art for the use thereof in the prophylaxis of mastitis, especially bovine mastitis.

Some documents, for example describe the use of "crude" unpurified vaccines for the prophylaxis of mastitis, which are based on the complete *S. uberis* bacterium or on protein extracts thereof.

Thus, in the article by Finch et al., Local vaccination with killed *Streptococcus uberis* protects the bovine mammary gland against experimental intramammary challenge with the homologous strain, Infect. Immun., 1994, 62, 3599-603, a study is disclosed wherein the vaccination of bovine livestock by intramammary administration of multiple doses of inactivated *S. uberis* bacteria allowed certain protection to be obtained in the animals against infections with subsequent homologous strains.

In the article by Hill et al., Immune modification of the pathogenesis of *Streptococcus uberis* mastitis in the dairy cow, FEMS Immunol. Med. Microbiol., 1994, 8, 109-118, the subcutaneous vaccination of cows is described with live *S. uberis* bacteria of the strain 014J and/or with a soluble extract derived from the same strain obtained by treatment of the bacteria with mutanolysin and type X hyaluronidase to eliminate the cell walls and capsules and subsequent elimination of the protoplasts by centrifugation. It was found that the treatment with only the soluble extract of *S. uberis* did not provide immunity to the animals, while the cows vaccinated by subcutaneous route with live bacteria in combination with the subsequent intramammary infusion of the bacterial extract did show a reduction in the incidence of mastitis.

A major part of the more recent studies relating to vaccines for *S. uberis* have focused on the search for specific bacterial subunits capable of providing protection against infections caused by *S. uberis*.

Thus, for example, in the international patent application WO-A-96/41879, the use of cohemolysin polypeptide of *S. uberis* (CAMP factor) in vaccines for the prevention and treatment of mastitis induced by *S. uberis* in lactating cows is disclosed.

In the article by Leigh et al., Vaccination with the plasminogen activator from *Streptococcus uberis* induces an inhibitory response and protects against experimental infection in the dairy cow, Vaccine, 1999, 17, 851-857, it is described how cows vaccinated by subcutaneous administration of a crude protein concentrate containing the plasminogen activator *S. uberis* (PauA), combined with an adjuvant, provided protection against the subsequent administration of a virulent strain of *S. uberis*.

In the international patent application WO-A-01/96381, the recombinant production of plasmin binding GapC proteins of *S. dysgalactiae*, *S. agalactiae*, *S. uberis*, *Streptococcus parauberis* and *Streptococcus iniae* is described as well as their use in vaccine compositions for the prevention and treatment of bacterial infections, particularly mastitis.

In the article by Prado et al., Vaccination of dairy cows with recombinant *Streptococcus uberis* adhesion molecule antibodies that reduce adherence to and internalization of *S. uberis* into bovine mammary epithelial cells, Vet. Immunol. Immunopathol., 2011, 141, 201-208, the use of the recombinant *S. uberis* adhesion molecule (SUAM) is suggested for the vaccination of dairy cows against mastitis due to the capacity observed in the antibodies generated to reduce the bacterium's adherence to the epithelial cells of the mammary gland in vitro.

In the international patent application WO-A-2010/041056, an immunogenic composition based on sortase proteins anchored to the *S. uberis* surface and its use as a prophylactic or therapeutic vaccine against infections caused by *S. uberis* is disclosed.

In the international patent application WO-A-2015/042449, vaccines against infections caused by *Streptococcus* are described comprising certain proteins of *S. uberis* as antigens, specifically the ferrichrome binding protein, the TU elongation factor, a lipoprotein and a serine protease.

At present, there is no vaccine on the European market with the specific indication for bovine mastitis caused by *S. uberis*. There is a vaccine called "*Streptococcus uberis* Bacterin" (product code 2851.00, of the company Hygieia Biological Laboratories (USA) which is marketed under a conditional license) on the US market. Said vaccine is based on a classic bacterin obtained from inactivated cultures of *S. uberis*, whose isolates come from clinical cases and for which the definitive marketing authorization is pending until the claims for bovine mastitis caused by *S. uberis* are endorsed by efficacy studies.

The remaining commercial vaccines against bovine mastitis caused, among others, by *S. uberis*, which are on the market, are polyvalent vaccines. These vaccines contain antigenic compositions based on a mixture of classic inactivated bacterins such as for example MASTIVAC® (Laboratorios Ovejero S.A., (Spain)): a polyvalent vaccine against bovine mastitis which is marketed in Spain and has a composition including bacterins from *Staphylococcus aureus*, *E. coli* J5, *S. agalactiae*, *S. dysgalactiae*, *S. uberis*, *Streptococcus pyogenes*, and *Arcanobacterium pyogenes*. Another example is Mastiplus® BR (Laboratório Vitafort Ind. e Com. de Productos Veterinários Ltda. (Brazil)) which is marketed in Brazil and in the composition of which are bacterins of *S. agalactiae*, *S. dysgalactiae*, *S. uberis*, *Staphylococcus aureus*, *Staphylococcus albus*, *E. coli*, *Arcanobacterium* (*Corynebacterium*) *pyogenes*, *Salmonella* sp., *Pseudomonas* sp., *Klebsiella* sp., *Bacillus subtilis*, *Aerobacter aerogenes*, and *Pasteurella bovis*. These vaccines do not solve the problem of clinical and subclinical mastitis caused by *S. uberis*, therefore novel developments and new vaccines are needed in order to fight against mastitis caused by the genus *Streptococcus* sp., and especially to fight specifically against *S. uberis*.

Thus, in spite of the different proposals available in the state of the art, there is still the need to provide new immunogenic products which are effective in preventing and/or treating infections caused by *Streptococcus* sp., particularly *S. uberis*, and especially which are effective for the prevention and/or treatment of mastitis in general, and of bovine mastitis in particular.

OBJECT OF THE INVENTION

The object of the present invention is a process for the preparation of an immunogenic agent.

Another aspect of the invention relates to an immunogenic agent comprising a biofilm from the culture of a biofilm-producing *S. uberis* strain.

Another aspect of the invention relates to an immunogenic agent obtainable by said process.

Another aspect of the invention relates to an immunogenic agent for use in the prevention and/or treatment of mastitis and/or infections caused by *Streptococcus* sp.

Another aspect of the invention relates to a vaccine comprising said immunogenic agent.

Another aspect of the invention is a vaccine for use in the prevention and/or treatment of mastitis and/or infections caused by *Streptococcus* sp.

Another aspect of the invention is a vaccine for use in the prevention and/or treatment of mastitis and/or infections caused by biofilm-producing bacteria.

Another aspect of the invention relates to a vaccination kit comprising the immunogenic agent or vaccine of the invention.

Another aspect of the invention relates to a pharmaceutical composition comprising teichoic acids for use in the prevention and/or treatment of mastitis and/or infections caused by *Streptococcus* sp.

Another aspect of the invention relates to a pharmaceutical composition comprising teichoic acids for use in the prevention and/or treatment of mastitis and/or infections caused by biofilm-producing bacteria.

DESCRIPTION OF THE DRAWINGS

In FIG. 1, the average of the temperature increase is depicted, as the ordinates, expressed in ° C., after 24 hours of the infection, in the vaccinated group (GV) and the control group (GC) which are depicted as the abscissas. It is observed that the vaccinated group shows a smaller temperature increase.

In FIG. 2, the mean value of $\log_{10}$ CFU/g of mammary tissue is depicted, as the ordinates, 24 hours after the infection in the vaccinated group (GV) and the control group (GC) which are depicted as the abscissas. It is observed that the group with lower *S. uberis* counts corresponds to the group vaccinated with the immunogenic agent of the invention.

In FIG. 3, the mean value of the affectation percentage of the infected gland is depicted 24 hours after the infection in the vaccinated group (GV) and the control group (GC) which are depicted as the abscissas. It is observed that the group with lower affectation corresponds to the group vaccinated with the immunogenic agent of the invention.

In FIG. 4, the average of the rectal temperature is depicted, as the ordinates, expressed in ° C. and as the abscissas the post-infection days (day 0 corresponds to the day of the infection) for the vaccinated group (■) and the control group (◇). A clear tendency to a reduction of the temperature in the vaccinated group during the days following the experimental infection was observed.

In FIG. 5, the mean value of $\log_{10}$ CFU/ml of milk is depicted, as the ordinates, during the post-infection days, which are depicted, as the abscissas, for the vaccinated group (■) and the control group (◇). It is observed that the group with lower *S. uberis* counts corresponds to the group vaccinated with the immunogenic agent of the invention. The day of the infection corresponds to day 0 of the abscissas axis.

In FIG. 6, the mean value of the milk production is depicted, as the ordinates, expressed in liters, after the infection (day 0) depicted as the abscissas, for the vaccinated group (■) and the control group (◇). It is clearly observed that, after the infection, the group vaccinated with the immunogenic agent of the invention shows a greater milk production than the control group almost daily basis.

In FIG. 7, the average value of somatic cells per ml of milk (SC/ml) is depicted, as the ordinates, during the post-infection days, depicted, as the abscissas, for the vaccinated group (■) and the control group (◇). The day of the infection corresponds to day 0. It is observed that on day 20 of the study the count of CS/ml of milk is clearly lower in the group vaccinated with the immunogenic agent of the invention compared with the control group. The results indicate that in spite of the fact that in both groups the count of somatic cells is increased, the vaccinated group returns to normal values significantly more quickly than the unvaccinated group.

In FIG. 8, optical densities at 595 nm corresponding to the in vitro culture of *S. uberis* in the presence of different concentrations (1:10 and 1:25 dilutions) of monoclonal antibodies anti-LTA and in the absence thereof (control group, GC) are shown. The results indicate that the presence of those monoclonal antibodies anti-LTA in the in vitro culture of *S. uberis* inhibits significantly the formation of biofilm in comparison to the culture in the absence of such monoclonal antibodies.

In FIG. 9, optical densities at 595 nm corresponding to the in vitro culture of *S. uberis* in the presence (vaccinated group, GV) and in the absence (control group, CG) of serum of an animal vaccinated with the immunogenic agent of the invention are shown. The results indicate that the presence of serum of an animal vaccinated with the immunogenic agent of the invention inhibits significantly the formation of biofilm under in vitro conditions by *S. uberis* in comparison to the culture in the absence of such serum.

DETAILED DESCRIPTION OF THE INVENTION

Figure 1:
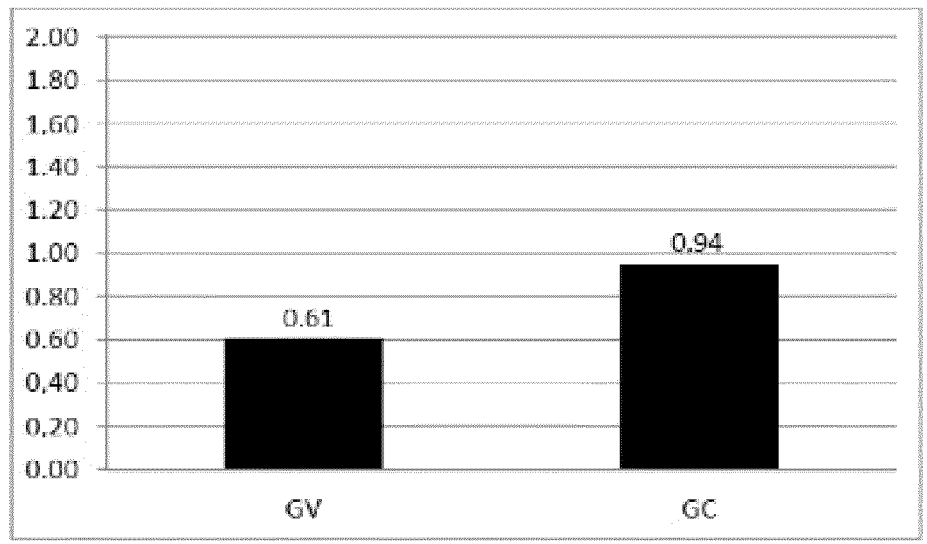
FIG. 1
Figure 2:
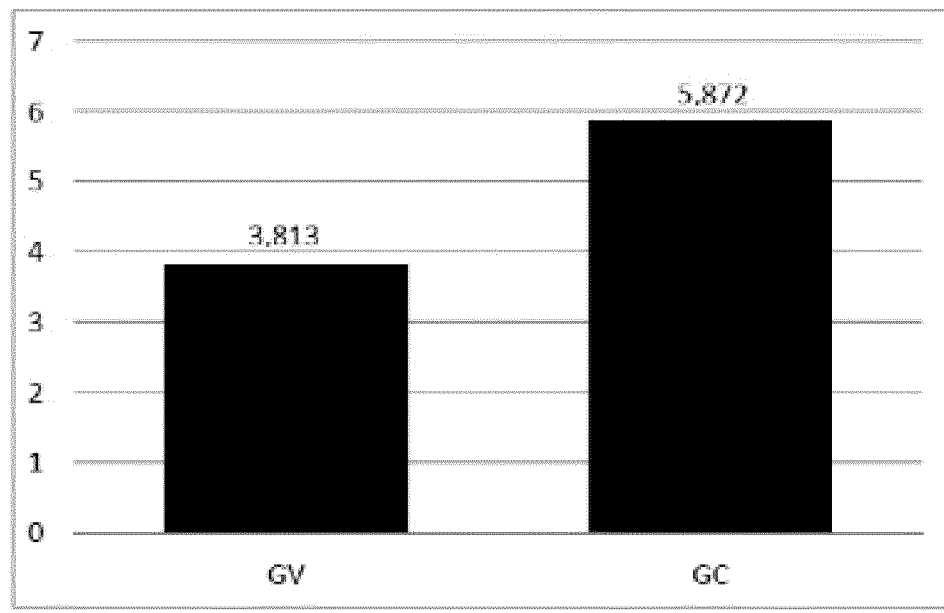
FIG. 2
Figure 3:
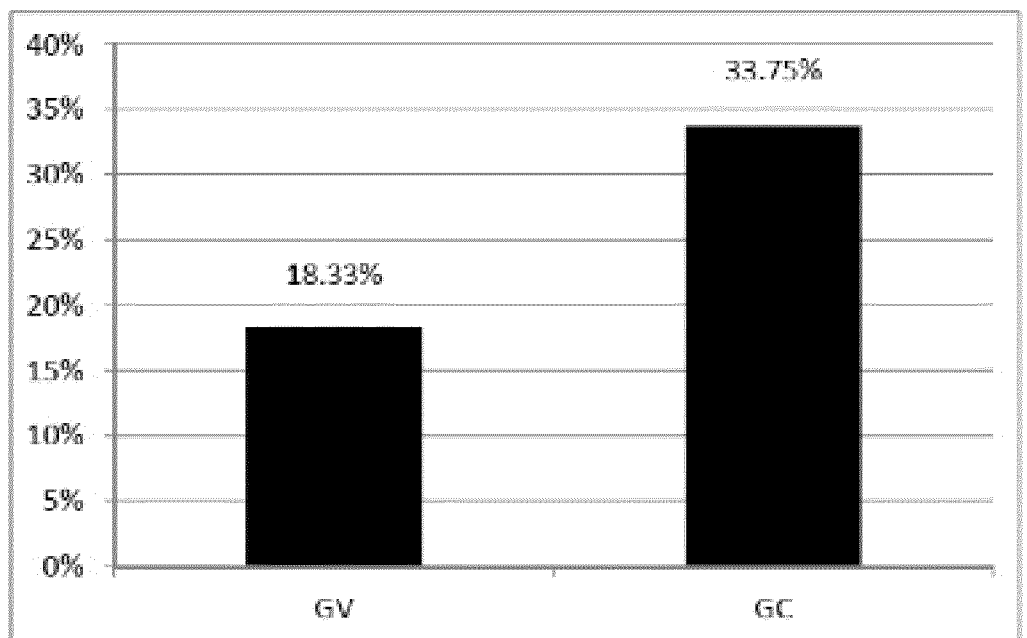
FIG. 3
Figure 4:
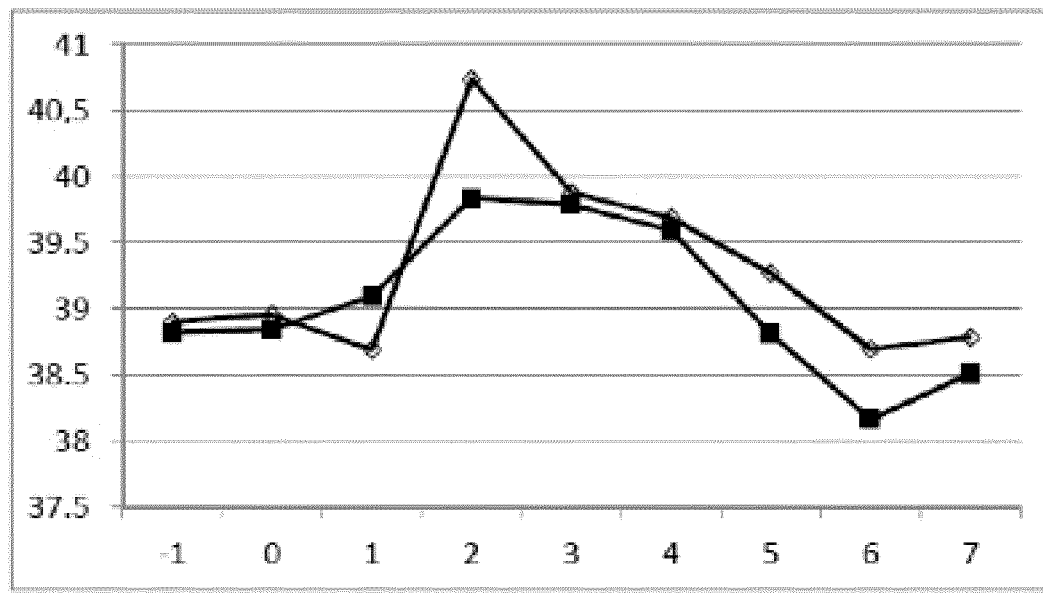
FIG. 4
Figure 5:
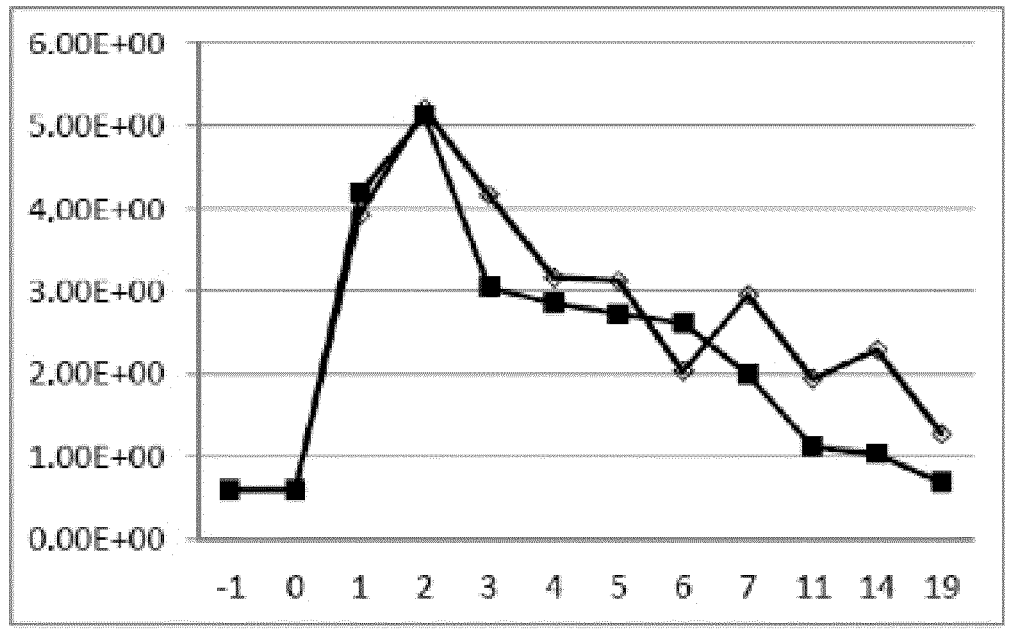
FIG. 5
Figure 6:
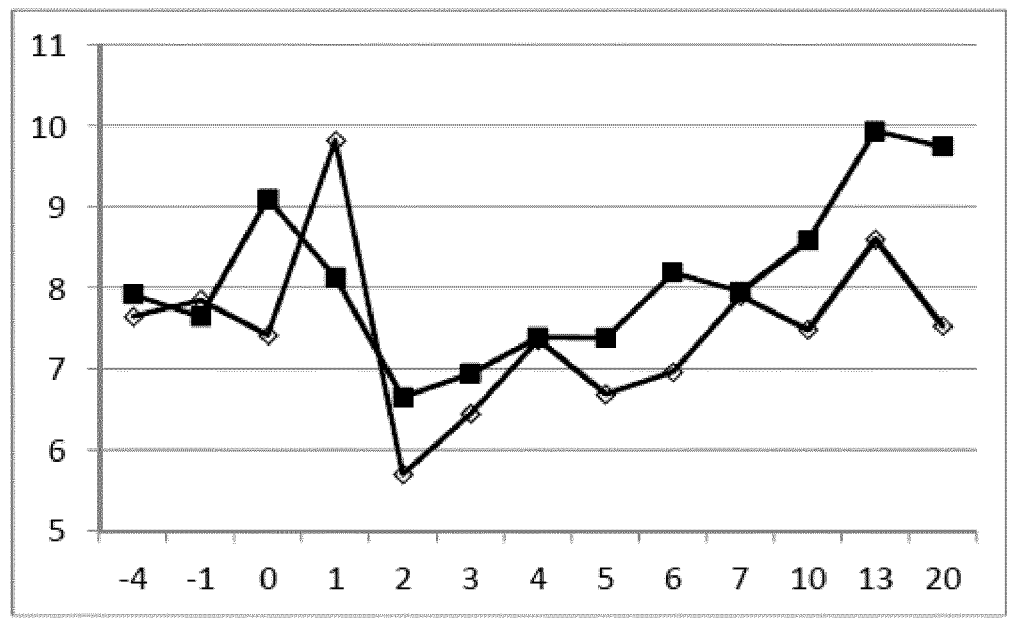
FIG. 6
Figure 7:
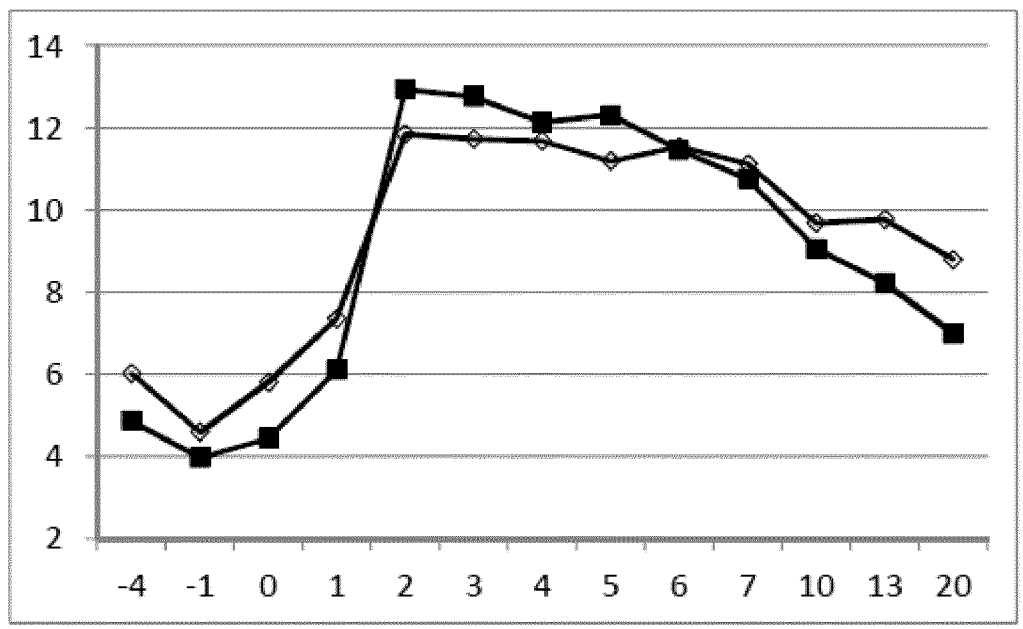
FIG. 7

The object of the present invention is a process for the preparation of an immunogenic agent which comprises the following steps:

a) incubating a biofilm-producing *S. uberis* strain to obtain a biofilm and b) subjecting the biofilm obtained in step a) to a thermal heat treatment.

The inventors of the present invention have developed a process for preparing a biofilm extract of *S. uberis* which, surprisingly, provides an immunogenic agent which is effective in vaccine compositions against infections caused by *Streptococcus* sp., especially for the prevention of mastitis caused by *S. uberis* in animals in general and in bovine livestock in particular.

Throughout the present description and in the claims, the expressions in singular preceded by the articles "a" or "the" are understood to also include, in a broad manner, the reference to the plural, unless the context clearly indicates the contrary.

In the context of the present invention, it is understood that the term "approximately" referred to a determined value indicates that a certain variation for said value is accepted, generally of +/−5%.

Process for the Preparation of the Immunogenic Agent

The present invention is based on the surprising finding that an immunogenic agent obtained from a biofilm of *S. uberis* bacterium and thermally treated has excellent immunogenic properties such that it is capable of inducing immunity in animals against infection by virulent *Streptococcus* sp., preferably *S. uberis*, strains, and by biofilm-producing bacteria.

A biofilm, as is well known by the person skilled in the art, is an aggregate of microorganisms, for example bacteria, which is formed adhered to a surface and which is covered by an extracellular matrix made of a mixture of polymeric compounds, mainly polysaccharides, which is generally known as an extracellular polymeric substance (EPS).

The composition of a biofilm basically comprises microbial cells, polysaccharides and water, among other extracellular products, which allow the matrix to be adapted to numerous micro-environments and situations, such as is described in I. W. Sutherland, *The biofilm matrix—an immobilized but dynamic microbial environment*, Trends in Microbiol., 2001, 9(5), 222-227.

In the process of the invention, a biofilm-producing *S. uberis* strain is used. Any *S. uberis* strain capable of producing a biofilm is suitable to be used in this process.

There are methods, well known by the person skilled in the art, for identifying the biofilm-producing bacteria. For example, the microplate test can be used and is described in G. E. Moore, *Biofilm production by Streptococcus uberis associated with intramammary infections*, 2009, University of Tennessee Honors Thesis Projects, or in Stepanovic et al., *Quantification of biofilm in microtiter plates: Overview of testing conditions and practical recommendations for assessment of biofilm production by staphylococci*, APMIS, 2007, 115, 891-899.

In step a) of the process of the invention, a biofilm-producing *S. uberis* strain is incubated to obtain a biofilm. As occurs with the biofilm-producing strains, said strain produces a biofilm during the incubation which is adhered to the surface of the receptacle wherein the process of the invention is carried out.

The bacteria can be incubated using a conventional culture medium, for example selected from the following: trypticase soy broth (TSB), trypticase soy agar (TSA), milk agar, among others, or mixtures thereof, all commercially available and well known by the person skilled in the art. Optionally, said mediums can be supplemented with additional ingredients such as for example, blood, yeast extract, glucose or casein, or mixtures thereof.

In a preferred embodiment of the invention, the culture medium comprises trypticase soy broth (TSB) containing tryptone and peptone soy. TSB is preferably supplemented with yeast extract (YE), more preferably TSB is used supplemented with yeast extract from 0.1% to 2%, more preferably from 0.5% to 1.5% and even more preferably supplemented with 1.2% of yeast extract, where the percentages are expressed in w/v.

The biofilm-producing *S. uberis* bacteria are generally incubated at conventional atmosphere, although the incubation is preferably carried out in an atmosphere comprising from 1% to 10% carbon dioxide, more preferably about 5% carbon dioxide.

The incubation takes place at a temperature generally comprised from 30° C. to 45° C., preferably from 35° C. to 40° C. and even more preferably at about 37° C.

The *S. uberis* bacteria are incubated for a period of time suitable for biofilm's development, generally for a period comprised from 24 hours (1 day) to 168 hours (7 days), preferably comprised from 36 hours (1.5 days) to 120 hours (5 days) and more preferably comprised from 48 hours (2 days) to 72 hours (3 days).

The biofilm-producing *S. uberis* strain can be incubated on any support or surface suitable for cell culture, as are well known by the person skilled in the art. For example, culture plates, culture bottles, well plates or culture tubes, among other possible supports, can be used. Said supports can be commercially obtained, for example by the company Corning or DDBiolab under the designation Falcon®.

The process of the invention can include an additional step after step a) which consists of recovering the biofilm from the culture medium which includes the bacterial cells remaining in suspension. In this optional step of the process, once the *S. uberis* biofilm has been formed, the culture medium together with the bacterial cells in suspension is removed by decantation and is discarded. The biofilm formed is recovered and is preserved for the following step.

In a preferred embodiment, the process of the invention includes an additional step after step a) and before step b) which consists of recovering the biofilm from the culture medium, a medium which includes the bacteria cells in suspension.

The biofilm produced by the *S. uberis* bacterial strain is generally adhered to the surface where it has been produced and must be detached from said surface. Detaching the biofilm from the surface can be simply carried out by physical means, for example with the help of a spatula or a deflaker, if it is needed.

Alternatively or additionally, a substance can be used to facilitate the detaching of the biofilm particularly a protease, which is added, typically, in the form of an aqueous solution on the biofilm in the same culture support by means of which the biofilm is detached from the surface and is obtained in the form of an aqueous suspension. Subsequently, it can be separated, for example by centrifugation.

Thus, in order to recover the biofilm, trypsin can also be used, typically in the form of an aqueous solution, with the aim of facilitating the detaching of the biofilm. In this way, the biofilm is recovered in the form of an aqueous suspension which contains trypsin in solution. The insoluble sedimented residue, formed by the biofilm, is separated by centrifugation and the supernatant, which contains the trypsin solution, is discarded.

In a preferred embodiment, the process of the invention includes an additional step after step a) and before step b) which consists of the use of trypsin for recovering the biofilm formed in step a). Optionally, the biofilm can be purified from trypsin solution, for example by means of a centrifugation procedure, typically at a speed equivalent from 10,000 g to 20,000 g for a period of time from 5 to 25 minutes, preserving the insoluble fraction.

In a preferred embodiment, the process of the invention includes a step wherein the recovered biofilm is suspended in an aqueous solution, typically in water for injection, although PBS or analogous buffered solutions can also be used, among others.

Subsequently, in step b) of the process of the invention, the biofilm obtained in the previous step a), preferably separated from the culture medium, and more preferably suspended in an aqueous solution, is subjected to a thermal treatment, tipically at a temperature comprised from 80° C. to 130° C., preferably comprised from 100° C. to 125° C. and more preferably at about 121° C. Said treatment generally takes place for a period comprised from 5 to 75 minutes, preferably comprised from 15 to 50 minutes and more preferably for about 45 minutes.

After step b), the process of the invention may include an additional step wherein the insoluble fraction is separated from the soluble extract. The insoluble fraction is discarded and the soluble extract comprising the immunogenic agent, resulting from the process of the invention, is preserved and which is surprisingly suitable for the treatment and/or prevention of mastitis and/or infections caused by *Streptococcus* sp., preferably *S. uberis*.

In a preferred embodiment, the process includes the step of discarding the insoluble fraction obtained following the thermal treatment of step b) and preserving the soluble extract comprising the immunogenic agent of the invention.

The separation of both fractions can be carried out, for example, by centrifugation, typically at a speed equivalent to from 10,000 g to 20,000 g for a period of time comprised from 5 to 30 minutes, preferably from 10 to 25 minutes.

The insoluble fraction typically contains the inactivated bacteria and insoluble components of the extracellular matrix. The supernatant comprises the soluble extract comprising the immunogenic agent resulting from the process of the invention.

This additional step contributes to provide a purer immunogenic agent, since it does not include the inactivated bacteria and the insoluble components of the extracellular matrix. The use of an immunogenic agent including said components, which can be removed, also generates an immunoprotective response, although the amount has to be adjusted in a manner well known by the person skilled in the art.

Optionally, the water can be removed, for example by lyophilization, by means of which the immunogenic agent is obtained in solid form, as a dry extract.

The Immunogenic Agent

Another aspect of the invention relates to the immunogenic agent obtainable by means of the process of the invention. Said immunogenic agent is referred hereinafter as the immunogenic agent of the invention.

An immunogenic agent comprising a thermally heat-treated biofilm, from the culture of a strain of biofilm-producing *S. uberis* is also part of the invention.

The immunogenic agent is preferably in the form of an aqueous suspension, aqueous solution or lyophilized.

An immunogenic product or agent, or antigen is understood as a component of a vaccine or pharmaceutical composition, which is capable of triggering an immune response when it is administered to an animal, which protects it against the subsequent infection by a pathogen and/or against the pathologies associated with said infection. It is understood that said immune response includes any type of immunity, whether cellular type or humoral type, as are well known by the person skilled in the art.

In the framework of the present invention, the term animal broadly refers to any animal susceptible to infections caused by *Streptococcus* sp., and in particular by *S. uberis*, more particularly it refers to mammals, including humans. Preferably, the animal is a ruminant, more preferably they are cows (or bovine), sheep (or ovine), pigs (or porcine) or goats (or caprine). In a particularly preferred embodiment, the immunogenic agent of the invention is used for the immunization of bovine cattle.

Said protective immune response can be determined by a lower susceptibility of the treated animals to subsequent infection by *S. uberis*, in particular to *S. uberis* strains different from those used for preparing said immunogenic product and/or to the associated pathologies thereof, particularly mastitis, comparatively with respect to the untreated animals.

As is shown in the efficacy tests which are disclosed in the Examples section, it is surprisingly confirmed that said agent is effective in the prevention of infections caused by *S. uberis*.

In particular, in said section, the results obtained when cows were vaccinated prior to the parturition the immunogenic agent of the invention are provided. A clear reduction of the temperature 2 days after the infection, a substantial reduction of the CFU/ml in milk, an increase in milk production in comparison to the control group and a lower count of somatic cells (SC/ml) in milk at the end of the study was observed.

The use of the immunogenic agent of the invention for the preparation of a vaccine for the prevention and/or treatment of mastitis and/or infections caused by *Streptococcus* sp., preferably for the prevention of mastitis and/or infections caused by *Streptococcus* sp. is thus an aspect of the invention.

In a preferred embodiment, the immunogenic agent of the invention is used for the preparation of a vaccine for the prevention and/or treatment of mastitis and/or infections caused by *S. uberis*, preferably for the prevention of mastitis and/or infections caused by *S. uberis*.

In another preferred embodiment, the immunogenic agent of the invention is used for the preparation of a vaccine for the prevention and/or treatment of clinical mastitis.

In another preferred embodiment, the immunogenic agent of the invention is used for the preparation of a vaccine for the prevention and/or treatment of subclinical mastitis.

The immunogenic agent of the invention for use in the prevention and/or treatment of mastitis and/or infections caused by *Streptococcus* sp., preferably for the prevention of mastitis and/or infections caused by *Streptococcus* sp; preferably for use in the prevention and/or treatment of mastitis and/or infections caused by *S. uberis*, preferably for the prevention of mastitis and/or infections caused by *S. uberis*; preferably for use in the prevention and/or treatment of clinical mastitis and/or subclinical mastitis is thus an aspect of the invention.

In the case of clinical mastitis, the following signs, among others, can be identified: inflammation of the mammary gland or a rectal temperature increase, appearance of visible abnormalities in the milk, such as protein aggregates or coagulates, possibly accompanied by pain and inflammation of the mammary gland, even the production of a secretion mainly made of protein aggregates, in non-vaccinated animals when compared with vaccinated animals. With respect to the subclinical signs of mastitis, the following, among others, can be indicated: inflammation of the mammary gland which does not create visible changes in the milk or udder, lower milk production and lower quality milk.

Inhibition of the Biofilm Formation by Teichoic Acids

The immunogenic agent of the invention is a product of complex composition. Said composition is determined by the process used in its preparation which includes the incubation of a biofilm-producing *S. uberis* strain to obtain a biofilm and the thermal treatment of the biofilm produced by said strain. Said agent comprises capsular polysaccharides and also, amongst the components, teichoic acids, such as lipoteichoic acids, have been identified. It is also observed a substantial increase in the presence of anti-LTA antibodies is detected in the plasma and in the milk in cows which have received a vaccine based on the immunogenic agent of the invention.

As disclosed in Brown et al., Wall Teichoic Acids of Gram-Positive Bacteria, Annu. Rev. Microbiol., 2013, 67, 313-336, teichoic acids include both lipoteichoic acids (LTA) which are anchored in the bacterial membrane via a glycolipid, and wall teichoic acids (WTA), which are covalently attached to peptidoglycan.

The lipoteichoic acids (LTA) are constituents of the cell wall of the Gram-positive bacteria, the structure of which varies as a function of the species, and generally they contain a long glycerol phosphate chain as a repeating unit which binds to the cell membrane by a glycolipid and can be additionally substituted with sugars and amino acids, particularly with D-alanine, for example as is described in the article by Czabanska et al., *Structural analysis of the lipoteichoic acids isolated from bovine mastitis Streptococcus uberis* 233, *Streptococcus dysgalactiae* 20333 *and Streptococcus agalactiae* 0250, Carbohydrate Res., 2012, 361, 200-205.

As shown in the examples, it is observed that the in vitro biofilm formation by *S. uberis* is significantly inhibited both in the presence of a monoclonal antibody anti-LTA and in the presence of serum from an animal vaccinated with the immunogenic agent of the invention.

Therefore, the inhibition of the biofilm formation by the presence of monoclonal antibodies anti-LTA and in the presence of serum from an animal vaccinated with the immunogenic agent of the invention produces an inhibition of the adhesion of the microorganism to the epithelial cells, and consequently reduces the probability of colonization/infection by *S. uberis*.

Thus, another aspect of the invention relates to a pharmaceutical composition comprising teichoic acids, preferably lipoteichoic acids, for use in the prevention and/or treatment of mastitis and/or infections caused by *Streptococcus* sp., preferably for use in the prevention of mastitis and/or infections caused by *Streptococcus* sp. In an embodiment of the invention, the pharmaceutical composition also comprises a pharmaceutically acceptable vehicle and/or a pharmaceutically acceptable adjuvant. Suitable vehicles and adjuvants are disclosed in the next section corresponding to vaccines.

In a preferred embodiment, the invention relates to a pharmaceutical composition comprising teichoic acids, preferably lipoteichoic acids, for use in the prevention and/or treatment of mastitis and/or infections caused by *S. uberis*, preferably for use in the prevention of mastitis and/or infections caused by *S. uberis*.

Another aspect of the invention relates to a pharmaceutical composition comprising teichoic acids, preferably lipoteichoic acids, for use in the prevention and/or treatment of mastitis and/or infections caused by biofilm-producing bacteria.

As already mentioned, there are methods, well known by the person skilled in the art, for identifying the biofilm-producing bacteria. Examples of biofilm-producing bacteria are, among others, *Streptococcus uberis, Pseudomonas aeruginosa, Staphylococcus epidermidis, Escherichia coli, Staphylococcus aureus, Enterobacter cloacae, Actenomyces israelii, Haemophilus influenza, Klebsiella pneumoniae,* and *Burholderia cepacia*.

In a preferred embodiment, the invention relates to a pharmaceutical composition comprising teichoic acids, preferably lipoteichoic acids, for use in the prevention and/or treatment of clinical mastitis.

In another preferred embodiment, the invention relates to a pharmaceutical composition comprising teichoic acids, preferably lipoteichoic acids, for use in the prevention and/or treatment of subclinical mastitis.

In a preferred embodiment, the pharmaceutical composition comprises lipoteichoic acids from *Streptococcus uberis*. In a more preferred embodiment, the lipoteichoic acids are from an immunogenic agent comprising a thermally heat-treated biofilm from the culture of a biofilm-producing *S. uberis* strain.

Vaccines

An aspect of the invention refers to a vaccine comprising an immunologically effective amount of the immunogenic agent of the invention.

Said vaccine is suitable for providing an immunoprotective response against infections caused by *S. uberis* and/or against the pathologies derived from infection by *S. uberis*, in particular against mastitis.

As shown in the experimental results provided in the examples, said vaccine is also suitable to inhibit biofilm formation of biofilm-producing bacteria.

The expression "immunologically effective" means that the amount of the immunogenic agent administered in the vaccination procedure, whether it is in one-single dose or in various doses, is sufficient for inducing an effective immunoprotective response in the vaccinated animal against an infection by virulent forms of *Streptococcus* sp., preferably *S. uberis*.

Said protective response can be assessed, for example by the absence or elimination of virulent bacteria or by the reduction of the number thereof in the vaccinated animals with respect to non-vaccinated animals, or by the absence of clinical signs of the infection, that is to say, no manifestation of any sign of clinical or subclinical mastitis, or by an attenuation or reduction of said signs in vaccinated animals. In the case of clinical mastitis, the following signs, among others, can be identified: inflammation of the mammary gland or rectal temperature increase, appearance of visible abnormalities in the milk, such as protein aggregates or coagulates, possibly accompanied by pain and inflammation of the mammary gland, even the production of a secretion mainly made of protein aggregates. With respect to the subclinical signs of mastitis, the following, among others, can be indicated: inflammation of the mammary gland which does not give visible changes in the milk or udder, lower milk production and lower quality milk.

Generally, the vaccine comprises an amount of the immunogenic agent of the invention comprised from 1 to 50 mg of dry extract per dose, preferably comprised from 2 to 25 mg per dose, and more preferably comprised from 4 to 12 mg per dose.

The immunologically effective amount of the antigen of the present invention can vary as a function of the species, the age and the weight of the animal to be vaccinated, also as a function of the health and physical condition thereof as well as of the mode of administration. Usually, the immunologically effective amount fluctuates within a particular range and the person skilled in the art does not have any difficulty in determining said amount by means of routine tests.

In an embodiment of the invention, the vaccine also comprises a pharmaceutically acceptable vehicle and/or a pharmaceutically acceptable adjuvant.

The carrier itself can also act as an adjuvant, particularly when the vaccine comprises an aqueous phase and an oily phase and it is in the form of an emulsion.

The vaccine is generally administered in liquid form, as a solution, emulsion or suspension; preferably it is in the form of an emulsion. It can also be in solid form which is dissolved, suspended or emulsified in a liquid vehicle prior to administration.

The vehicles suitable for preparing the vaccine in liquid form include water, or an isotonic saline solution, that is to say, with a salt concentration equal to that of the physiological cellular medium, or an oil, or the culture liquid wherein the bacteria are cultured, or the mixtures thereof.

Additionally, if it is desired, the vehicle can include other auxiliary substances or pharmaceutically acceptable excipients such as for example wetting agents, dispersant agents, emulsifying agents, buffer agents (for example phosphate buffer), stabilizing agents such as carbohydrates (for example glucose, sucrose, mannitol, sorbitol, starch or dextrans), or proteins (for example albumin, casein, bovine serum or skimmed milk).

The physical-chemical characteristics of the excipients as well as the name of the commercial products under which they are marketed can be found in the book R. C. Rowe et al., Handbook of Pharmaceutical Excipients, $4^{th}$ edition, Pharmaceutical Press, London, 2003 [ISBN: 0-85369-472-9].

The adjuvants, as is well known in the art, are nonspecific stimulants of the immune system which, administered together with the antigen, make the immunological response more effective. Some examples of adjuvants are: aluminum hydroxide, aluminum phosphate, aluminum oxide, muramyl dipeptides, vitamin E, squalane, squalene, ginseng, zymosan, glucans, dimethylaminoethyl-dextran, dextrans, non-ionic block polymers, monophosphoryl lipid A, vegetable oil, saponins, complete Freund's adjuvant, incomplete Freund's adjuvant, W/O, O/W, W/O/W type emulsions and mixtures thereof.

Emulsions are defined as the dispersion of a liquid making the dispersed phase, into a second liquid which is the continuous phase wherein the first phase is not miscible; in particular the phases are water and oil. Emulsions can be of the W/O, O/W, W/O/W type as a function of the type of surfactant used as the emulsifier and also as a function of the relation between the two phases.

In an embodiment of the invention, the vaccine is in the form of an emulsion such that it comprises an aqueous phase, an oily phase and a surfactant which acts as an emulsifying agent. The immunogenic agent of the invention is typically dissolved in the aqueous phase.

In a particularly preferred embodiment, the vaccine comprises an adjuvant based on a combination of a mineral oil and a product obtained from a fatty acid and a sugar alcohol such as for example those marketed by the company SEP-PIC under the commercial designation Montanide™. Emulsions of the W/O/W type can be prepared with said adjuvant.

The vaccine preferably also comprises an additional adjuvant which is selected from among aluminum hydroxide, aluminum phosphate, aluminum oxide, muramyl dipeptides, vitamin E, squalane, squalene, ginseng, zymosan, glucans, dimethylaminoethyl-dextran, dextrans, non-ionic block polymers, monophosphoryl lipid A, saponins and mixtures thereof.

In a more preferred embodiment of the invention, the vaccine comprises monophosphoryl lipid A.

Monophosphoryl lipid a (MPLA or MPL) is a known adjuvant for the formulation of vaccines which is obtained from bacterial lipopolysaccharides, normally from the lipopolysaccharide of *Salmonella minnesota*, for example like the one commercially available by the company SIGMA under the designation "Lipid A, monophosphoryl from *Salmonella minnesota* Re 595 (Re mutant)" (product L 6895). In the context of the present invention, monophosphoryl lipid A also includes the derivatives and synthetic analogues thereof which are also suitable as adjuvants. Among the derivatives of monophosphoryl lipid A used as adjuvants, the derivative 3-deacylated (3D-MPL or 3D-MPLA) stands out, for example the one commercially available by company SIGMA under the designation MPL™. Synthetic analogues of monophosphoryl lipid A can also be used, for example, those described in the patent application WO2008/153541-A1 or those commercially available by companies Avanti Polar Lipids (product PHAD™) or AdipoGen (product AG-CU1-0002).

The vaccine can be administered by the following routes: oral, topical, transdermal, transmucosal, intradermal, subcutaneous, intramuscular, intraperitoneal, intravenous or intramammary, preferably it is administered by the following routes: intradermal, subcutaneous, intramuscular, intraperitoneal, intravenous or intramammary, more preferably it is administered by intramuscular route.

Said vaccine can be prepared according to the normal process used by the person skilled in the art for the preparation of pharmaceutical formulations suitable for the different forms of administration as is described for example in the manual Remington The Science and Practice of Pharmacy, 20$^{th}$ edition, Lippincott Williams & Wilkins, Philadelphia, 2000 [ISBN: 0-683-306472].

The normal volume of a dose of an injectable vaccine like the one of the invention is comprised from 0.5 mL to 5 mL, preferably from 1 mL to 3 mL and more preferably from 1 mL to 2 mL.

As is described in the efficacy tests of the examples, the vaccine according to the present invention is effective in the protection of pregnant-lactating cows against infection by *S. uberis* virulent strains, as is confirmed by a clear reduction in bacteria count in the milk 14 and 19 days after the infection and by an improvement in the clinical signs of mastitis. The vaccine is also effective in an experimental model in rabbits, a reduction of the clinical signs and a remarkable reduction in *S. uberis* count in the mammary tissue being observed at 24 hours or at 48 hours after the infection, with respect to non-vaccinated animals.

A reduction of the *S. uberis* count in the mammary tissue has also been observed at 24 hours post-infection in animals vaccinated with the vaccine of the invention, in comparison with animals vaccinated with a classic bacterin, obtained from a *S. uberis* strain inactivated by formaldehyde treatment.

Another aspect of the invention therefore refers to a vaccine comprising the immunogenic agent of the invention for the use thereof in the prevention and/or treatment of mastitis and/or infections caused by *Streptococcus* sp.; preferably for use in the prevention of mastitis and/or infections caused by *Streptococcus* sp.

In a preferred embodiment, the invention relates to a vaccine for use in the prevention and/or treatment of mastitis and/or infections caused by *S. uberis*, preferably for use in the prevention of mastitis and/or infections caused by *S. uberis*.

In another preferred embodiment, the invention relates to a vaccine for use in the prevention and/or treatment of mastitis and/or infections caused by biofilm-producing bacteria.

In another preferred embodiment, the invention relates to a vaccine for use in the prevention and/or treatment of clinical mastitis.

In another preferred embodiment, the invention relates to a vaccine for use in the prevention and/or treatment of subclinical mastitis.

In the framework of the present invention, the term prevention relates to the administration of the vaccine with a preventive or prophylactic aim, that is to say, aimed at preventing or delaying the appearance of mastitis and/or infections caused by *Streptococcus* sp, in particular by *S. uberis* or aimed at reducing its incidence. The term treatment relates to the administration of the vaccine with a therapeutic aim, that is to say, aimed at eliminating, reducing, improving or alleviating the symptoms of mastitis and/or infection by *Streptococcus* sp, in particular by *S. uberis* when these have already been shown.

In the framework of the present invention, mastitis and/or infections caused by *Streptococcus* sp, in particular by *S. uberis* as has been previously indicated, relate to its effect in general on any animal which is susceptible to infections caused by *Streptococcus* sp, in particular by *S. uberis*, typically mammals, preferably ruminants, more preferably cows (or bovine), sheep (or ovine), pigs (or porcine) or goats (or caprine).

In a preferred embodiment, the vaccine comprising the immunogenic agent of the invention is used for the prevention and/or treatment of mastitis in bovine livestock (or bovine mastitis), more preferably mastitis caused by *S. uberis* and even more preferably it is used for the prevention and/or treatment of bovine mastitis in dairy cows.

Animals can be vaccinated at any suitable time. Thus the vaccine can be administered in a prophylactic manner to those animals which have the risk of being infected by *Streptococcus* sp., in particular by *S. uberis*.

In a particularly preferred embodiment, the vaccine which comprises the immunogenic agent of the invention is prophylactically used for the prevention of mastitis.

The vaccine can be administered in one or more dose. A multiple-dose vaccination, as is well known in the art, consists of administering a first immunizing dose, followed by one or more additional doses which act as booster doses. The number of doses and the time interval between them which are most suitable for the vaccination can be determined according to routine tests.

In an embodiment of the invention, the vaccine is of single-dose administration.

In another embodiment of the invention, the vaccine is administered in more than one dose, preferably in 2 or in 3 doses, more preferably in 3 doses. The different doses are preferably administered with a time interval between them comprised from 10 to 70 days, more preferably from 20 to 60 days.

The vaccine can further comprise a combination of the immunogenic agent obtainable by the process of the invention with one or more additional immunogenic agents.

The immunogenic agents which can be combined with the immunogenic agent of the invention include: *Streptococcus agalactiae, Streptococcus dysgalactiae, Escherichia coli, Klebsiella* sp., *Mycoplasma bovis* and *Staphylococcus aureus*, among others, preferably *S. agalactiae, S. aureus* and/or *E. coli*.

Another aspect of the invention relates to a pharmaceutical composition comprising teichoic acids, preferably lipoteichoic acids, for use as a vaccine in the prevention and/or treatment of mastitis and/or infections caused by *Streptococcus* sp., preferably for use as a vaccine in the prevention of mastitis and/or infections caused by *Streptococcus* sp.

In a preferred embodiment, the invention relates to a pharmaceutical composition comprising teichoic acids, preferably lipoteichoic acids, for use as a vaccine in the prevention and/or treatment of mastitis and/or infections caused by *S. uberis*, preferably for use as a vaccine in the prevention of mastitis and/or infections caused by *S. uberis*.

Another aspect of the invention relates to a pharmaceutical composition comprising teichoic acids, preferably lipoteichoic acids, for use as a vaccine in the prevention and/or treatment of mastitis and/or infections caused by biofilm-producing bacteria.

In a preferred embodiment, the invention relates to a pharmaceutical composition comprising teichoic acids, preferably lipoteichoic acids, for use as a vaccine in the prevention and/or treatment of clinical mastitis.

In another preferred embodiment, the invention relates to a pharmaceutical composition comprising teichoic acids, preferably lipoteichoic acids, for use as a vaccine in the prevention and/or treatment of subclinical mastitis.

Vaccination Kit

Another aspect of the present invention relates to a vaccination kit for vaccinating animals against infection by S. uberis and especially for vaccinating animals against mastitis.

Said vaccination kit comprises a container comprising an immunologically effective amount of the immunogenic agent of the invention or the vaccine of the invention.

In a preferred embodiment, said immunogenic agent or said vaccine are in a single ready-to-use container.

In a preferred embodiment, the immunogenic agent is in lyophilized form.

In another preferred embodiment, the kit also comprises a second container containing a pharmaceutically acceptable vehicle or diluent. This embodiment is especially appropriate in the case of using the immunogenic agent in lyophilized form.

In another preferred embodiment, the kit also comprises an informative manual or leaflet which contains the information for the administration of the immunogenic agent or vaccine of the invention.

The vaccination kit for use in the prevention and/or treatment of mastitis and/or infections caused by Streptococcus sp. or biofilm-producing bacteria, preferably for the prevention of mastitis and/or infections caused by Streptococcus sp. or biofilm-producing bacteria; preferably for use in the prevention and/or treatment of mastitis and/or infections caused by S. uberis, preferably for the prevention of mastitis and/or infections caused by S. uberis; preferably for use in the prevention and/or treatment of clinical mastitis and/or subclinical mastitis is thus an aspect of the invention and preferably accompanied by an informative manual or leaflet containing the information for the administration of the immunogenic agent or vaccine of the invention.

The invention comprises the following embodiments:

1. A process for the preparation of an immunogenic agent, characterized in that it comprises the following steps:
   a) incubating a biofilm-producing S. uberis strain to obtain a biofilm, and
   b) subjecting the biofilm obtained in step a) to a thermal heat treatment.
2. The process according to embodiment 1, characterized in that the incubation is carried out at an atmosphere comprised from 1% to 10% carbon dioxide.
3. The process according to embodiment 1 or 2, characterized in that in step a) the culture medium is TSB supplemented with yeast extract from 0.1 to 2% w/v.
4. The process according to any one of embodiments 1 to 3, characterized in that in step a) the culturing takes place at a temperature of between 30° C. and 45° C.
5. The process according to any one of embodiments 1 to 4, characterized in that in step a) the culturing is carried out for a period comprised from 24 hours to 168 hours.
6. The process according to any one of embodiments 1 to 5, characterized in that in step b) the thermal treatment is carried out at a temperature comprised from 80° C. to 130° C.
7. The process according to any one of embodiments 1 to 6, characterized in that in step b) the thermal treatment is carried out for a period of time comprised from 5 to 75 minutes.
8. The process according to any one of embodiments 1 to 7, characterized in that it comprises an additional step after step a) and before step b) which consists of recovering the biofilm from the culture medium.
9. The process according to embodiment 8, characterized in that trypsin is used for recovering the biofilm formed in step a).
10. The process according to embodiment 8 or 9, characterized in that the recovered biofilm is suspended in an aqueous solution.
11. The process according to any one of embodiments 1 to 10, characterized in that it includes the step of discarding the insoluble fraction obtained after the thermal treatment of step b) and preserving the soluble extract.
12. An immunogenic agent obtainable by the process of any one of embodiments 1 toll.
13. An immunogenic agent comprising a thermally heat-treated biofilm from the culture of a biofilm-producing S. uberis strain.
14. The immunogenic agent according to embodiment 12 or 13, characterized in that it is in the form of an aqueous suspension, aqueous solution or lyophilized.
15. The immunogenic agent according to any one of embodiments 12 to 14 for use in the prevention and/or treatment of mastitis and/or infections caused by Streptococcus sp.
16. The immunogenic agent according to embodiment 15 for use in the prevention of mastitis and/or infections caused by Streptococcus sp.
17. The immunogenic agent according to embodiment 15 or 16, characterized in that Streptococcus sp. is S. uberis.
18. The immunogenic agent according to embodiment 15 or 17 for use in the prevention and/or treatment of clinical mastitis.
19. The immunogenic agent according to embodiment 15 or 17 for use in the prevention and/or treatment of subclinical mastitis.
20. A vaccine comprising an immunologically effective amount of the immunogenic agent of any of embodiments 12 to 14.
21. The vaccine according to embodiment 20, characterized in that it also comprises a pharmaceutically acceptable vehicle and/or a pharmaceutically acceptable adjuvant.
22. The vaccine according to embodiment 20 or 21, characterized in that it is in the form of an emulsion, suspension or solution.
23. The vaccine according to embodiment 21, characterized in that it comprises an adjuvant selected from aluminum hydroxide, aluminum phosphate, aluminum oxide, muramyl dipeptides, vitamin E, squalane, squalene, ginseng, zymosan, glucans, dimethylaminoethyl-dextran, dextrans, nonionic block polymers, monophosphoryl lipid A, saponins and mixtures thereof.
24. The vaccine according to embodiment 23, characterized in that it comprises monophosphoryl lipid A.
25. The vaccine according to any one of embodiments 20 to 24, characterized in that it comprises an additional immunogenic agent.

26. The vaccine according to embodiment 25, characterized in that it comprises an additional immunogenic agent selected from the group consisting of: *Streptococcus agalactiae, Staphylococcus aureus, Klebsiella* sp., *Mycoplasma bovis* and *Escherichia coli*.
27. The vaccine according to any of embodiments 20 to 26, characterized in that it is administered by intradermal, subcutaneous, intramuscular, intraperitoneal, intravenous or intermammary route.
28. The vaccine according to embodiment 27, characterized in that it is administered by the intramuscular route.
29. The vaccine according to any of embodiments 20 to 28, characterized in that it is administered in one or more than one dose.
30. The vaccine according to embodiment 29, characterized in that it is administered in 2 or 3 doses.
31. The vaccine according to any one of embodiments 20 to 30 for use in the prevention and/or treatment of mastitis and/or infections caused by *Streptococcus* sp.; preferably for use in the prevention of mastitis and/or infections caused by *Streptococcus* sp.
32. The vaccine according to embodiment 31 for use in the prevention and/or treatment of mastitis and/or infections caused by *S. uberis*, preferably for use in the prevention of mastitis and/or infections caused by *S. uberis*.
33. The vaccine according to any one of embodiments 20 to 30 for use in the prevention and/or treatment of mastitis and/or infections caused by biofilm-producing bacteria.
34. The vaccine according to any one of embodiments 31 to 33 for use in the prevention and/or treatment of clinical mastitis.
35. The vaccine according to any one of embodiment 31 to 33 for use in the prevention and/or treatment of subclinical mastitis.
36. A vaccination kit characterized in that it comprises a container comprising an immunologically effective amount of the immunogenic agent of any of embodiments 12 to 14 or the vaccine of any of embodiments 20 to 26.
37. The kit according to embodiment 36, characterized in that the immunogenic agent or the vaccine is in a single container ready-to-use.
38. The kit according to embodiment 36, characterized in that the immunogenic agent is in lyophilized form.
39. The kit according to embodiment 38, characterized in that it also comprises a second container which contains a pharmaceutically acceptable vehicle or diluent.
40. The kit according to any one of embodiments 36 to 39, characterized in that it also comprises an informative manual or leaflet which contains the information for the administration of the immunogenic agent of any of embodiments 12 to 14 or of the vaccine of any of embodiments 20 to 26.
41. A pharmaceutical composition comprising teichoic acids for use in the prevention and/or treatment of mastitis and/or infections caused by *Streptococcus* sp., preferably *S. uberis*.
42. A pharmaceutical composition according to embodiment 41 for use in the prevention of mastitis and/or infections caused by *Streptococcus* sp., preferably *S. uberis*.
43. A pharmaceutical composition comprising teichoic acids for use in the prevention and/or treatment of mastitis and/or infections caused by biofilm-producing bacteria.
44. A pharmaceutical composition according to any one of embodiments 41 to 43 for use in the prevention and/or treatment of clinical mastitis.
45. A pharmaceutical composition according to any one of embodiments 41 to 43 for use in the prevention and/or treatment of subclinical mastitis.
46. A pharmaceutical composition according to any one of embodiments 41 to 45, characterized in that the teichoic acids are lipoteichoic acids.
47. A pharmaceutical composition according to embodiment 46, characterized in that the lipoteichoic acids are from *Streptococcus uberis*.
48. A pharmaceutical composition according to embodiment 47, characterized in that the lipoteichoic acids are from an immunogenic agent comprising a thermally heat-treated biofilm from the culture of a biofilm-producing *S. uberis* strain.
49. A pharmaceutical composition comprising teichoic acids for use as a vaccine in the prevention and/or treatment of mastitis and/or infections caused by *Streptococcus* sp., preferably *S. uberis*.
50. A pharmaceutical composition according to embodiment 49 for use as a vaccine in the prevention of mastitis and/or infections caused by *Streptococcus* sp., preferably *S. uberis*.
51. A pharmaceutical composition comprising teichoic acids for use as a vaccine in the prevention and/or treatment of mastitis and/or infections caused by biofilm-producing bacteria.
52. A pharmaceutical composition according to any one of embodiments 49 to 51 for use as a vaccine in the prevention and/or treatment of clinical mastitis.
53. A pharmaceutical composition according to any one of embodiments 49 to 51 for use as a vaccine in the prevention and/or treatment of subclinical mastitis.
54. A pharmaceutical composition according to any one of embodiments 49 to 53, characterized in that the teichoic acids are lipoteichoic acids.
55. A pharmaceutical composition according to embodiment 54, characterized in that the lipoteichoic acids are from *Streptococcus uberis*.
56. A pharmaceutical composition according to embodiment 55, characterized in that the lipoteichoic acids are from an immunogenic agent comprising a thermally heat-treated biofilm from the culture of a biofilm-producing *Streptococcus* sp., preferably *S. uberis* strain.

EXAMPLES

Example 1 Preparation of the Immunogenic Agent

The strain 5616 of *S. uberis* was used in the process to prepare the immunogenic agent of the invention, which is a field isolate obtained from a case of clinical bovine mastitis in Spain. This strain was a biofilm producer, as was checked in the microplate test described in G. E. Moore, Biofilm production by *Streptococcus uberis* associated with intramammary infections, 2009, University of Tennessee Honors Thesis Projects.

An inoculation was firstly prepared suspending the lyophilized bacteria in water for sterile injection until a concentration of $10^9$ bacteria/ml was obtained, subsequently infecting a culture medium TSB+0.5% YE with said suspension according to a proportion 1/100 and incubating for 16 h at 37° C.

A 225 cm$^2$ Falcon® type cellular culture bottle (DDBiolab) was then infected with 100 ml of a mixture with a proportion 1:100 prepared with the inoculation previously prepared and TSB+0.5% YE culture medium and was incubated for 4 days in an oven at 37° C. and at an atmosphere with a content of about 5% carbon dioxide.

Once the culturing was completed, the medium was removed from the culture bottle, including the bacterial cells in suspension and 40 ml of a trypsin aqueous solution was added (trypsin solution 1×, Sigma-Aldrich) and was maintained for 15 minutes under agitation at a temperature of 37° C.

The content of the bottle was emptied and the suspension obtained was centrifuged at 15,300 g for 15 minutes, the supernatant being discarded.

The sedimented residue was resuspended in 0.5 ml of water for injection and said suspension was then heated to 121° C. for 45 minutes. It was then centrifuged at 15,300 g for 15 minutes and the supernatant was preserved, while the sedimented residue was discarded.

The supernatant solution was freeze-dried in order to obtain the dry immunological agent.

Example 2 Efficacy Test of the Vaccine in Pregnant-Lactating Rabbits

A group of 20 pregnant rabbits were immunized by subcutaneous administration of 1 ml of a vaccine containing a solution of the immunogenic agent obtained by a process analogous to the one described in Example 1, at a rate of a concentration of 4 mg/ml, formulated with an oily adjuvant of the Montanide™ (SEPPIC) series in a proportion of aqueous solution:adjuvant 1:1 at days 13 and 27 of pregnancy. The differences were compared with a 20-rabbits control group. The infection was carried out by the intramammary route by injection of 100 μl of a suspension of a virulent *S. uberis* strain at a rate of $10^3$ CFU/ml, 15-20 days post-partum of the last rabbit.

In order to determine the efficacy of the vaccine, the following parameters were determined for the vaccinated and infected animals in relation to the non-vaccinated and infected control group: rectal temperature, count of CFU/g of tissue at 24 hours post-infection and local clinical signs in the infected mammary gland.

The experimental data were statistically processed by SPSS 14.0 program. An ANOVA analysis was carried out if the results followed a normal distribution; otherwise non-parametric tests were used such as the Mann-Whitney U Test or Chi-squared Test in the case of 2 groups.

The results clearly demonstrated the efficacy of the immunogenic agent of the invention for preventing infections caused by *S. uberis*, since it was observed:

- A reduction of the average of the temperature 24 hours after infection (FIG. 1),
- A reduction of the CFU/g of tissue at 24 hours after infection (FIG. 2), and
- A reduction in the affectation of the affected gland after infection (FIG. 3)

Example 3 Efficacy Test of the Vaccine in Pregnant-Lactating Cows

A group of 10 pregnant cows were immunized which were administered, by the intramuscular route, 2 ml of a vaccine containing the immunogenic agent obtained by a process analogous to the one described in Example 1, at a rate of a concentration of 4 mg/ml, formulated with an oily adjuvant of the Montanide™ (SEPPIC) series in a proportion of aqueous solution:adjuvant 1:1, 31 and 10 days prior to the estimated parturition date. The differences were compared with a control group formed by 10 cows. The infection took place by the intramammary route by injection of 5 ml of a suspension of a virulent *S. uberis* strain at a rate of $10^2$ CFU/ml, 16 days after the estimated parturition date.

In order to determine the efficacy of the vaccine, the following parameters were determined for the vaccinated and infected animals in relation to the non-vaccinated and infected control group: the rectal temperature, the counts of CFU/ml and SC/ml (SC=somatic cells) in milk post-infection and the local clinical signs in the infected mamma.

The serological response induced in the immunized cows was also analyzed using the experimental vaccine. The serums were analyzed by ELISA to detect the presence of antibodies against *S. uberis*.

In order to check the safety of the vaccination, the possible clinical signs observed in the cows were assessed after the immunization. The clinical signs and calves' mortality after birth were also assessed in order to disregard a possible negative effect of the vaccination on the animals.

The experimental data were statistically processed by SPSS 14.0 program. An ANOVA analysis was carried out if the results followed a normal distribution; otherwise non-parametric tests were used such as the Mann-Whitney U Test or Chi-squared Test in the case of 2 groups.

In relation to the rectal temperature during the vaccination, no differences were observed between the groups during the days prior to the vaccination and revaccination, nor during the three subsequent days when the temperature was recorded.

The results clearly demonstrated the efficacy of the immunogenic agent of the invention for preventing infections caused by *S. uberis* since the following was observed after infection in the vaccinated group with respect to the control group:

- A reduction of the temperature 2 days after infection (FIG. 4),
- A reduction of the CFU/ml in milk (FIG. 5),
- An increase of milk production in comparison to the control group (FIG. 6), and
- A lower count of somatic cells (SC/ml) in milk at the end of the study (FIG. 7).

Therefore, it can be concluded that the immunogenic agent of the invention is effective in preventing mastitis caused by *S. uberis*, and is suitable for the prevention and/or treatment of mastitis and/or infections caused by *Streptococcus* sp., preferably *S. uberis*.

Example 4 Inhibition of In Vitro Biofilm Production by the Presence of Monoclonal Antibodies Anti-LTA in Cultures of *S. uberis*

In this test *S. uberis* strain was cultured in the presence of four concentrations of monoclonal antibody anti-LTA in a 96-well microplate following substantially the methodology disclosed in Stepanovic et al., (op. cit.).

In this study *S. uberis* strain, referenced as 5616, was used. TSB+0.5% YE was used to propagate and culture the strain at pH 7.5 in an incubator set at 37° C. and 5% $CO_2$ for 20 h and 24 h respectively.

The monoclonal antibody anti-LTA was purchased from Hycult Biotech (The Netherlands), catalog Nr. HM2048, showing a concentration of >200 μg/ml, in a culture medium with a low endotoxin level containing 0.02% sodium azide.

The monoclonal antibody dilutions used in this test were: 1:10, 1:25, 1:50 and 1:100.

A control culture of *S. uberis* without the presence of monoclonal antibody was also prepared.

Strains were incubated in the wells without shaking. For each reference 8 wells were used.

After incubation, optical density at 550 nm was recorded to check the ability of growth of the microorganisms. No significant differences were seen between the groups.

Afterwards, wells were decanted and washed with PBS (pH 7.3) and dried about 1 h at 37° C. Dried tubes were stained with crystal violet (0.1%). Excess stain was removed and wells were washed with sterile water.

Dyestuff was solubilized with ethanol 95% and optical density at 595 nm was recorded to assess the inhibition of the biofilm production.

The results obtained for each group are shown in Table I:

TABLE I

| Group | $OD_{595}$ |
|---|---|
| MAB 1:10 | 0.503* |
| MAB 1:25 | 0.975* |
| MAB 1:50 | 1.216 |
| MAB 1:100 | 1.265 |
| Control group (GC) | 1.138 | wherein * shows that results were statistically significant at p values < 0.05 in comparison to the control group according to one factor ANOVA analysis using software SPSS v22 (IBM Analytics).

Figure 8:
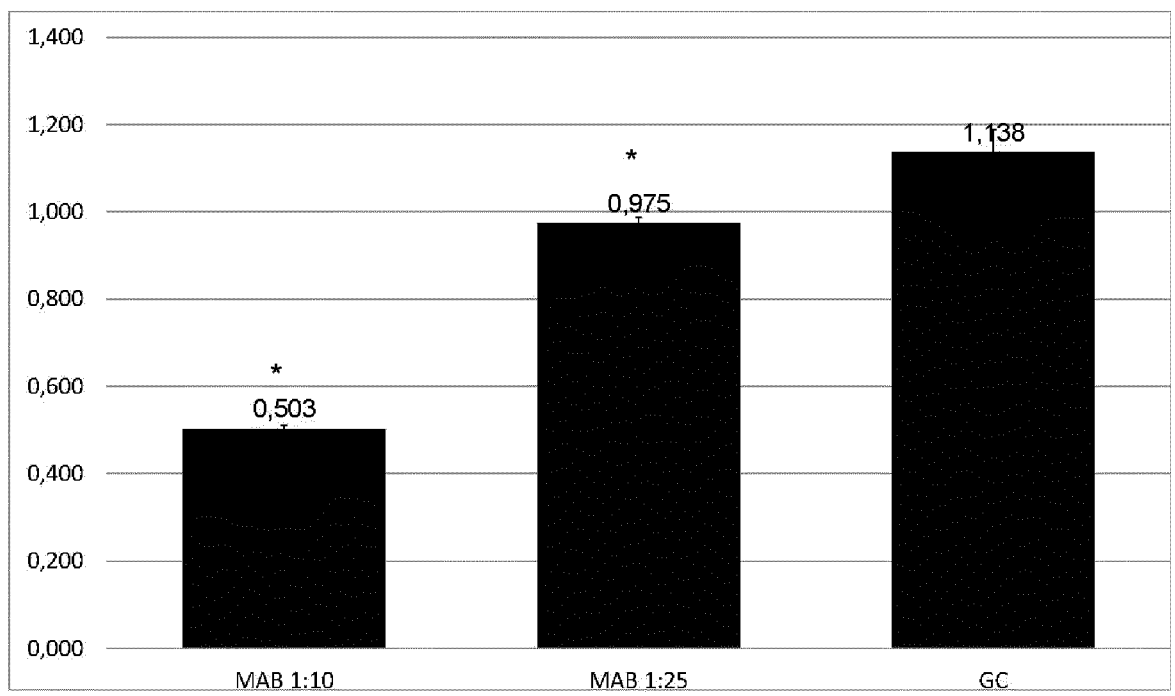
FIG. 8

In FIG. 8, optical densities at 595 nm corresponding to the in vitro culture of *S. uberis* in the presence of different concentrations (1:10 to 1:25 dilutions) of monoclonal antibodies anti-LTA and in the absence thereof (control group, GC) are represented.

The results indicate that the presence of those monoclonal antibodies anti-LTA in the culture at 1:10 and 1:25 dilutions inhibits significantly the formation of biofilm under in vitro conditions in comparison to the culture in the absence of such monoclonal antibodies.

Example 5 Inhibition of In Vitro Biofilm Production by the Presence of Serum from an Animal Vaccinated with the Immunogenic Agent of Example 1 in Cultures of *S. uberis*

In this test *S. uberis* strain was cultured in the presence of serum from an animal vaccinated with the immunogenic agent of Example 1. *S. uberis* strain, referenced as 5616, was used in this study. TSB+0.5% YE was used to propagate and culture the strain at pH 7.5 in an incubator set at 37° C. and 5% $CO_2$ for 20 h and 24 h respectively.

Serum from an animal vaccinated with the immunogenic agent following the procedure disclosed in Example 3 was used at a dilution of 1:2000 in the reference designated as vaccinated group (GV).

A control culture (GC) of *S. uberis* without the presence of serum from a vaccinated animal was also prepared.

Strains were incubated in the wells without shaking. For each reference 8 wells were used.

After incubation, optical density at 550 nm was recorded to check the ability of growth of the microorganisms. No significant differences were seen between the two groups.

Afterwards, wells were decanted and washed with PBS (pH 7.3) and dried about 1 h at 37° C. Dried tubes were stained with crystal violet (0.1%). Excess stain was removed and wells were washed with sterile water.

Dyestuff was solubilized with ethanol 95% and optical density at 595 nm was recorded to assess the inhibition of the biofilm production.

Figure 9:
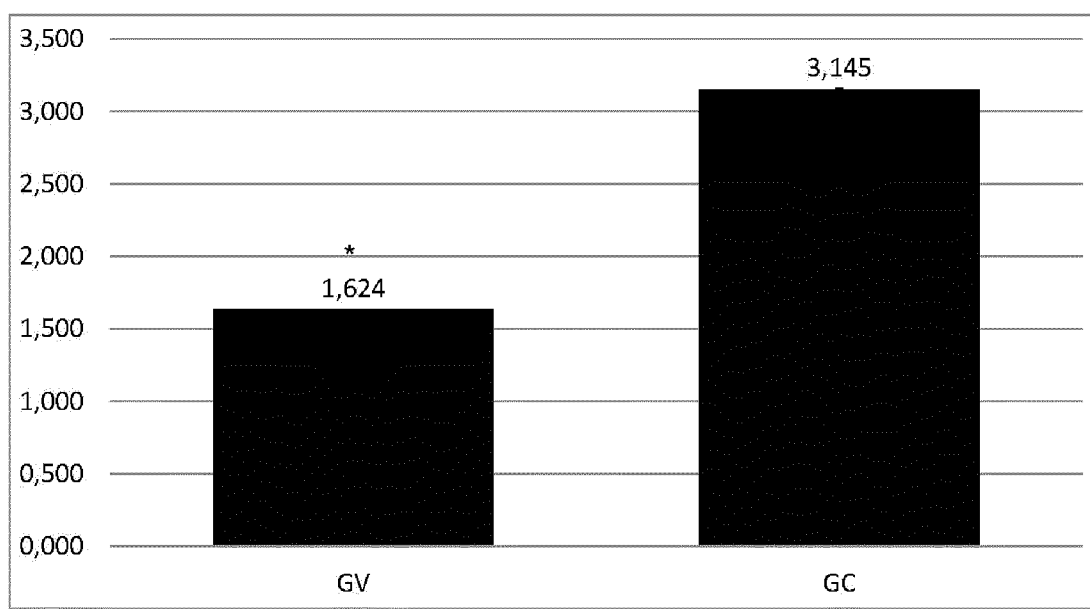
FIG. 9

In FIG. 9, optical densities at 595 nm corresponding to the in vitro culture of *S. uberis* in the presence (vaccinated group, GV) and in the absence (control group, CG) of serum of an animal vaccinated with the immunogenic agent of the invention are represented.

The results indicate that the presence of serum of an animal vaccinated with the immunogenic agent of the invention inhibits significantly (p value<0.05, t-student test) the formation of biofilm under in vitro conditions in comparison to the culture in the absence of such serum.

The invention claimed is:

1. An immunogenic agent comprising a soluble extract of a heat-treated biofilm, wherein the soluble extract of the heat-treated biofilm is obtained by a process comprising:
    a) incubating a biofilm-producing *S. uberis* strain in a culture medium to obtain a biofilm,
    b) recovering the biofilm from the culture medium and discarding the culture medium and bacterial cells in suspension,
    c) subjecting the biofilm obtained in step b) to a heat treatment carried out at a temperature comprised from 80° C. to 130° C., and,
    d) discarding the insoluble fraction obtained after the heat treatment of step c) and preserving the soluble extract, wherein the soluble extract of the heat-treated biofilm thereby is the immunogenic agent.

2. A vaccine comprising an immunologically effective amount of the immunogenic agent of claim 1.

3. The vaccine according to claim 2, characterized in that it further comprises a pharmaceutically acceptable vehicle and/or a pharmaceutically acceptable adjuvant.

4. The vaccine according to claim 3, characterized in that it comprises an adjuvant selected from aluminum hydroxide, aluminum phosphate, aluminum oxide, muramyl dipeptides, vitamin E, squalane, squalene, ginseng, zymosan, glucans, dimethylaminoethyl-dextran, dextrans, non-ionic block polymers, monophosphoryl lipid A, saponins and mixtures thereof.

5. The vaccine according to claim 2, characterized in that it is administered by an intradermal, subcutaneous, intramuscular, intraperitoneal, intravenous or intramammary route.

6. The vaccine according to claim 2, characterized in that it is administered in more than one dose.

7. The vaccine according to claim 2, characterized in that it comprises an additional immunogenic agent from a microorganism selected from the group consisting of: *Streptococcus agalactiae*, *Staphylococcus aureus*, *Klebsiella* sp., *Mycoplasma bovis* and *Escherichia coli*.

8. A process for the preparation of an immunogenic agent, characterized in that it comprises the following steps:
    a) incubating a biofilm-producing S. uberis strain in a culture medium to obtain a biofilm,
    b) recovering the biofilm from the culture medium and discarding the culture medium and bacterial cells in suspension,
    c) subjecting the biofilm obtained in step b) to a heat treatment carried out at a temperature comprised from 80° C. to 130° C., and,
    d) discarding the insoluble fraction obtained after the heat treatment of step c) and preserving the soluble extract, wherein the soluble extract of the heat-treated biofilm thereby is the immunogenic agent.

9. The process according to claim 8, characterized in that the incubation is carried out at an atmosphere comprising from 1% to 10% carbon dioxide.

* * * * *